(12) United States Patent
Lauritsch et al.

(10) Patent No.: US 9,013,471 B2
(45) Date of Patent: Apr. 21, 2015

(54) 3D X-RAY IMAGING OF CORONARY VESSELS WITH ECG GATING AND MOTION CORRECTION

(75) Inventors: Günter Lauritsch, Nürnberg (DE); Christopher Rohkohl, Erlangen (DE)

(73) Assignee: Siemens Aktiengesellschaft, München (DE)

( * ) Notice: Subject to any disclaimer, the term of this patent is extended or adjusted under 35 U.S.C. 154(b) by 88 days.

(21) Appl. No.: 13/152,367

(22) Filed: Jun. 3, 2011

(65) Prior Publication Data

US 2011/0298793 A1 Dec. 8, 2011

(30) Foreign Application Priority Data

Jun. 4, 2010 (DE) .......................... 10 2010 022 791

(51) Int. Cl.
*G06T 15/00* (2011.01)
*A61B 6/00* (2006.01)
*G06T 11/00* (2006.01)

(52) U.S. Cl.
CPC .............. *A61B 6/504* (2013.01); *A61B 6/4441* (2013.01); *A61B 6/5264* (2013.01); *A61B 6/5288* (2013.01); *A61B 6/541* (2013.01); *G06T 11/005* (2013.01); *G06T 2211/412* (2013.01); *G06T 2211/424* (2013.01)

(58) Field of Classification Search
USPC ........... 345/419, 648, 27, 649, 652, 653, 655, 345/660, 663, 664, 666, 672, 678, 679, 345/681; 382/130, 131
See application file for complete search history.

(56) References Cited

U.S. PATENT DOCUMENTS

| 5,710,875 | A | * | 1/1998 | Harashima et al. ........... 345/419 |
| 6,070,097 | A | | 5/2000 | Bahner et al. |
| 7,415,093 | B2 | | 8/2008 | Edic et al. |
| 7,500,784 | B2 | | 3/2009 | Grebner |
| 7,948,503 | B2 | * | 5/2011 | Shekhar et al. ............... 345/648 |
| 2006/0074292 | A1 | * | 4/2006 | Thomson et al. ............. 600/411 |
| 2006/0120507 | A1 | | 6/2006 | Brunner |

(Continued)

FOREIGN PATENT DOCUMENTS

DE 102004048209 B3 9/2005

OTHER PUBLICATIONS

Shekhar et al., "Mutual Information-Based Rigid and Nonrigid Registration of Ultrasound Volumes," Jan. 2002, IEEE Transactions on Medical Imaging, vol. 21, No. 1, pp. 9-22.*

(Continued)

*Primary Examiner* — Xiao M. Wu
*Assistant Examiner* — Steven Elbinger

(57) ABSTRACT

A method for three-dimensional visualization of a moving structure by a rotation angiography method is described. A series of projection images is recorded by an image acquisition unit from different recording angles during a rotation cycle. A three-dimensional image data can be reconstructed from the projection images. A continuous rotation cycle is proposed to be performed with simultaneous recording of at least one ECG. A three-dimensional reconstructed reference image is generated through a first correction of the motion of the moving structure by affine transformations. A three-dimensional image data of the moving structure is reconstructed from the data acquired in the continuous rotation cycle when using the reconstructed reference image while performing an estimation and correction of the motion by elastic deformations.

8 Claims, 4 Drawing Sheets

(56) References Cited

U.S. PATENT DOCUMENTS

| | | | |
|---|---|---|---|
| 2006/0133564 A1* | 6/2006 | Langan et al. ................ 378/8 |
| 2009/0263001 A1* | 10/2009 | Ding et al. ................ 382/131 |
| 2009/0292818 A1* | 11/2009 | Blount et al. ............. 709/231 |
| 2010/0020926 A1* | 1/2010 | Boese et al. ................ 378/44 |
| 2010/0278405 A1* | 11/2010 | Kakadiaris et al. ........ 382/131 |

OTHER PUBLICATIONS

Rohling et al., "Automatic registration of 3-D ultrasound images," Jan. 4-7, 1998, Sixth International Conference on Computer Vision, pp. 298-303.*

Zagrodsky et al., "Multi-function extension of simplex optimization method for mutual information based registration of ultrasound volumes," in Proc. SPIE, vol. 4322, Medical Imaging, Feb. 17, 2001, pp. 508-515.*

Schäfer et al.; "Motion-compensated and gated cone beam filtered back-projection for 3-D rotational X-ray angiography"; IEEE Trans Med Imaging. Jul. 2006; 25(7): pp. 898-906.

Christophe Blondel et al; "Reconstruction of Coronary Arteries From a Single Rotational X-Ray Projection Sequence"; IEEE Transactions on Medical Imaging, IEEE Service Center, Piscataway, NJ, US LNKD-DOI:10.1109/TMI.2006.873224, vol. 25, No. 5, May 2006; pp. 653-663.

Scherl et al.; "Fast GPU-Based CT Reconstruction using the Common Unified Device Architecture (CUDA)"; In: Frey, Eric C. (Eds.) Nuclear Science Symposium, Medical Imaging Conference 2007 (2007 Nuclear Science Symposium, Medical Imaging Conference Honolulu, Hawaii (USA) 30.10.-Mar. 11, 2007) vol. 6 2007, pp. 4464-4466—ISBN 978-1-4244-0922-8.

Christopher Rohkohl et al.; "Interventional 4-D Motion Estimation and Reconstruction of Cardiac Vasculature without Motion Periodicity Assumption"; pp. 1-8.

Eberhard Hansis et al.; "Evaluation of Iterative Sparse Object Reconstruction From Few Projections for 3-D Rotational Coronary Angiography"; IEEE Transactions on Medical Imaging, vol. 27, No. 11, Nov. 2008; pp. 1-8.

Eberhard Hansis et al.; "Four-Dimensional Cardiac Reconstruction from Rotational X-ray Sequences—First Results for 4D Coronary Angiography"; SPIE vol. 7258, No. 1, pp. 1-11, Mar. 2009.

Eberhard Hansis et al.; "Projection-based motion compensation for gated coronary artery reconstruction from rotational x-ray angiograms"; Phys. Med. Biol. 53 (2008) pp. 3807-3820.

* cited by examiner

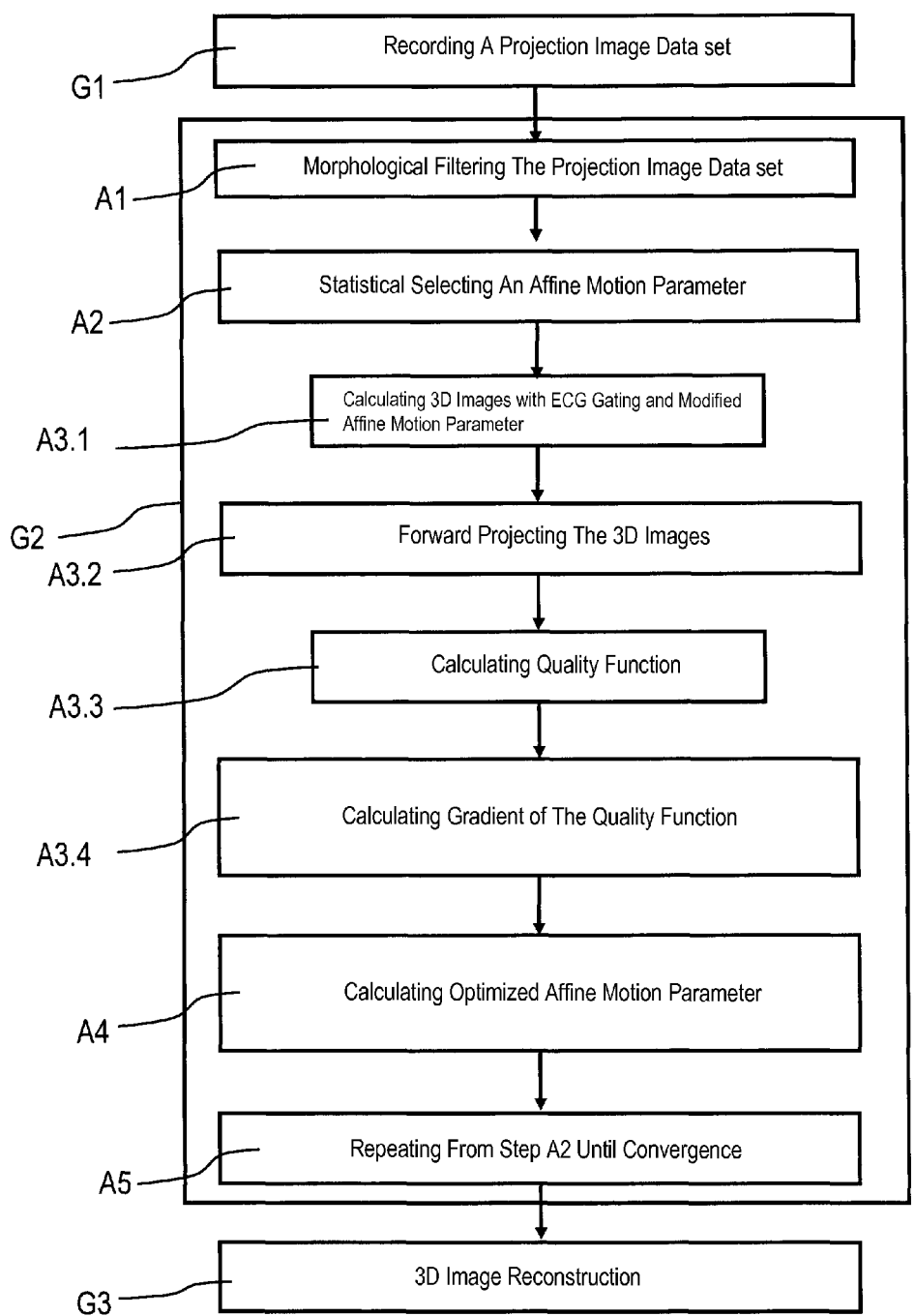

3D X-RAY IMAGING OF CORONARY VESSELS WITH ECG GATING AND MOTION CORRECTION

CROSS REFERENCE TO RELATED APPLICATIONS

This application claims priority of German application No. 10 2010 022 791.9 filed Jun. 4, 2010, which is incorporated by reference herein in its entirety.

FIELD OF THE INVENTION

The invention relates to a method for three-dimensional imaging of coronary vessels with ECG gating and motion correction.

BACKGROUND OF THE INVENTION

Three-dimensional rotation angiography (3D rotation angiography) is a standard method used for estimating the vascular anatomy before and during interventions. The reconstruction algorithms used for 3D reconstruction of the cardiac blood vessels by means of rotation angiography are heavily dependent on the periodicity of the cardiac motion. In the interventional environment patients often have arrhythmic heart signals or cannot hold their breath during a complete acquisition.

For diagnostic examination purposes and for interventional procedures in for example cardiology, radiology and neurosurgery, interventional X-ray systems are used for imaging, the typical essential features of which systems can be a C-arm on which an X-ray tube and an X-ray detector are mounted, a patient positioning table, a high-voltage generator for generating the tube voltage, a system control unit, and an imaging system including at least one monitor. The C-arm can be held for example by means of a robot arm. A C-arm X-ray system of this kind, as illustrated for example in FIG. 1, has a C-arm 2 which is rotatably mounted on a stand in the form of a six-axis industrial or articulated-arm robot 1 and at the ends of which are mounted an X-ray radiation source, for example an X-ray tube assembly 3 with X-ray tube and collimator, and an X-ray image detector 4 as image acquisition unit.

The articulated-arm robot 1 known for example from U.S. Pat. No. 7,500,784 B2, which preferably has six axes of rotation and hence six degrees of freedom, enables the C-arm 2 to be moved to an arbitrary position in space, for example by being rotated around a center of rotation between the X-ray tube assembly 3 and the X-ray detector 4. The inventive X-ray system 1 to 4 can be rotated in particular around centers of rotation and axes of rotation in the C-arm plane of the X-ray image detector 4, preferably around the center point of the X-ray image detector 4 and around axes of rotation intersecting the center point of the X-ray image detector 4.

The known articulated-arm robot 1 has a base frame which is permanently installed on a floor for example. Attached thereto is a carousel which is rotatable about a first axis of rotation. Mounted on the carousel so as to be pivotable about a second axis of rotation is a robot rocker arm to which is attached a robot arm which is rotatable about a third axis of rotation. Mounted at the end of the robot aim is a robot hand which is rotatable about a fourth axis of rotation. The robot hand has a retaining element for the C-arm 2, said retaining element being pivotable about a fifth axis of rotation and rotatable about a sixth axis of rotation running perpendicular thereto.

The X-ray diagnostic apparatus is not dependent on the industrial robot for its implementation. Conventional C-arm devices can also be used.

The X-ray image detector 4 can be a rectangular or square, flat semiconductor detector which is preferably produced from amorphous silicon (a-Si). Integrating and possibly counting CMOS detectors can also be used, however.

A patient 6 to be examined is placed as the examination subject in the beam path of the X-ray tube assembly 3 on a patient positioning table 5 so that images of the heart, for example, can be recorded. Connected to the X-ray diagnostic apparatus is a system control unit 7 having an imaging system 8 which receives and processes the image signals from the X-ray image detector 4 (control elements are not shown, for example). The X-ray images can then be viewed on a monitor 9.

Body electrodes 10 which are placed for example on the thorax of the patient 6 can record the ECG signals of the patient 6 and transmit them to the system control unit 7.

A respiration sensor 11 for recording the respiratory motion of the patient 6 lying on the patient positioning table 5, which sensor can be for example a chest belt placed around the thorax of the patient 6, measures the respiratory motion of the patient 6 and transmits it to the system control unit 7.

The X-ray tube assembly 3 emits a bundle of rays 12 originating from a beam focus of its X-ray radiation source and striking the X-ray image detector 4. If it is intended to generate 3D data sets according to the so-called DynaCT method for low-contrast visualization of for example soft tissue, as described for example in US 2006-0120507 A1, the rotatably mounted C-arm 2 with X-ray tube assembly 3 and X-ray image detector 4 is rotated in such a way that, as FIG. 2 shows schematically in a view onto the axis of rotation, the X-ray tube assembly 3 represented figuratively here by its beam focus as well as the X-ray image detector 4 move around an examination subject 13 located in the beam path of the X-ray tube assembly 3 on an orbit 14. The orbit 14 can be traversed completely or partly for the purpose of generating a 3D data set.

In this case the C-arm 2 with X-ray tube assembly 3 and X-ray image detector 4 moves according to the DynaCT method preferably through an angular range of at least 180°, for example 180° plus fan angle, and records projection images in rapid succession from different projections. The reconstruction can be carried out based on just a subset of said acquired data.

The subject 13 to be examined can be for example an animal or human body or indeed a phantom body.

The X-ray tube assembly 3 and the X-ray image detector 4 each rotate about the object 5 in such a way that the X-ray tube assembly 3 and the X-ray image detector 4 are disposed on opposite sides of the subject 13.

In normal radiography or fluoroscopy by means of an X-ray diagnostic apparatus of this type the medical 2D data of the X-ray image detector 4 is buffered in the imaging system 8 if necessary and subsequently displayed on the monitor 9.

By applying the methods of computed tomography (CT) it is aimed to generate a 3D image of the coronary vessels from the 2D projection data of a moving heart. For this purpose it is important to take into account the movement of the heart. Particularly in the case of the long recording times of the C-arm systems of at least 5 s other movements can also take place in addition to the beating motion of the heart. While periodic motions (heartbeat) can be frozen by means of ECG gating, non-periodic motions such as for example arrhythmic heartbeat, respiration or patient movement must be estimated and corrected in the reconstruction.

With ECG gating, a specific cardiac phase can be singled out from the recording data. The recording time of conventional CT scanners is currently in the region of about 100-200 ms, such that within a single heartbeat all of the measurement data required for reconstructing a 3D image for a specific cardiac phase can be recorded. Since the recording time of C-arm systems is about 5 s, measurement data of a plurality of cardiac cycles must be used for reconstructing a 3D image for a specific cardiac phase, as is described for example in Schäfer et al [1]. An assumption of ECG gating is the periodicity of the motion. With long recording times the periodicity is no longer guaranteed due to arrhythmic heartbeat, respiration, patient motion.

Furthermore gaps in the recording data are produced as a result of ECG gating. There are approaches aimed at using all the measurement data of an image acquisition by correcting the motion of the heart in the reconstruction step. Estimating the motion from the recorded image data represents a challenge. Motion estimation is a very poorly formulated problem. The degrees of freedom of a general motion are very great and cannot be clearly determined from the measured recording data.

In the publication by C. Blondel et al [3] the motion estimation problem is limited based on the assumption that the motion is periodic, although this is not the case in reality.

E. Hansis et al [5], Rohkohl et al [6] and H. Scherl et al [7] also take non-periodic motions into account in their estimation. The complexity of motion estimation is limited through use of an a priori 3D image. A search is made for a motion in order to reconstruct a 3D image which is very similar to the a priori 3D image. Typically the a priori 3D image is generated from a reconstruction using ECG gating. With non-periodic motion, the image quality of the a priori 3D image and consequently also the image quality of the main reconstruction suffer.

U.S. Pat. No. 7,415,093 B2 describes a CT cardiac diagnostic imaging method which uses a priori information from motions from 3D ultrasound examinations using ECG gating. ECG and ultrasound data of the heart is acquired in real-time during a scan. A data acquisition module is controlled during the scan so as to predictively control the acquisition of the CT data as a function of the real-time ECG data and the real-time ultrasound data. A 3D image is reconstructed from the acquired CT data. The motion field is estimated from the ultrasound examinations and used as a priori knowledge.

DE 10 2004 048 209 B3 discloses a precise and comparatively easy-to-implement method for generating a three-dimensional image data set of a moving object by means of X-ray tomography as well as a device that is particularly suitable for performing the method and has a rotatably mounted X-ray tube assembly detector unit as well as an evaluation unit, wherein it is provided to group a number of two-dimensional raw images according to a cyclical relative time, to generate at least two preliminary 3D image data sets in each case from raw images corresponding to one another according to said grouping, to derive at least one motion matrix by comparison in each case of two preliminary 3D image data sets used as source data set and target data set, to generate a motion-compensated 3D image data set corresponding to a reference time of the source data set through application of the or each motion matrix onto the associated target data set, and to sum the or each motion-compensated 3D image data set with at least one further motion-compensated 3D image data set or another preliminary 3D image data set corresponding to the same reference unit. The motion field is therefore estimated from first preliminary 3D images from different cardiac phases (time instants). The method has the disadvantage that if there is considerable movement no usable first preliminary 3D images can be generated.

U.S. Pat. No. 6,070,097 A describes a method for generating a gating signal for cardiac examinations by means of an MRI system comprising a detector system which receives an ECG signal from a scanned patient and generates a gating signal when a detected peak in the ECG signal meets a set of R-wave criteria which include a specified positive slope on the leading segment of the detected peak, a minimum duration of the leading segment, a specified negative slope on the segment trailing the detected peak and a minimum peak amplitude. An ECG signal is therefore analyzed in order to detect the QRS pulse at which ECG gating is to take place.

SUMMARY OF THE INVENTION

The object of the invention is to provide a method for three-dimensional imaging of coronary vessels with ECG gating and motion correction.

According to the invention the object is achieved by a method disclosed in the independent claim. Advantageous embodiments are disclosed in the dependent claims.

The object is achieved according to the invention by means of a method for three-dimensional visualization of a moving structure by means of a rotation angiography method in which a series of projection images is recorded from different recording angles by an image acquisition unit during a rotation cycle for the purpose of 3D data acquisition, wherein three-dimensional image data can be reconstructed from the projection images, the following steps being performed:
a) performance of a continuous rotation cycle with simultaneous recording of at least one ECG,
b) generation of a three-dimensional reconstructed reference image through a first correction of the motion of the moving structure by means of affine transformations, and
c) reconstruction of three-dimensional image data of the moving structure from the data acquired in step a) when using the precorrected reference image from b) while performing an estimation and correction of the motion by means of elastic deformations.

According to an embodiment of the invention a morphological filter is applied to the 2D projection data for the purpose of reducing anatomical noise.

According to another embodiment of the invention the filter is a top-hat filter.

According to a further embodiment of the invention an affine transformation is applied.

According to another embodiment of the invention patient motion and respiration are described as a motion model by means of translation and rotation.

According to a further embodiment of the invention arrhythmic cardiac motions are described by means of affine motion models.

According to another embodiment of the invention the motion field associated with a first provisional 3D image is estimated from the 2D projection images of the data recording directly by iterative comparison of a forward projection of a 3D image and the measured 2D recording.

According to a further embodiment of the invention the 3D data acquisition is performed by means of DynaCT.

By virtue of these inventive features a first provisional 3D image can be generated even given considerable movement. The associated motion field is estimated from the 2D projection images of the data recording for example by means of DynaCT directly through iterative comparison of a forward projection of a 3D image and the measured 2D recording.

BRIEF DESCRIPTION OF THE DRAWINGS

The invention is explained in more detail below with reference to exemplary embodiments illustrated in the drawing, in which:

FIG. 4 shows the execution sequence of the method according to the invention.

DETAILED DESCRIPTION OF THE INVENTION

Figure 1:
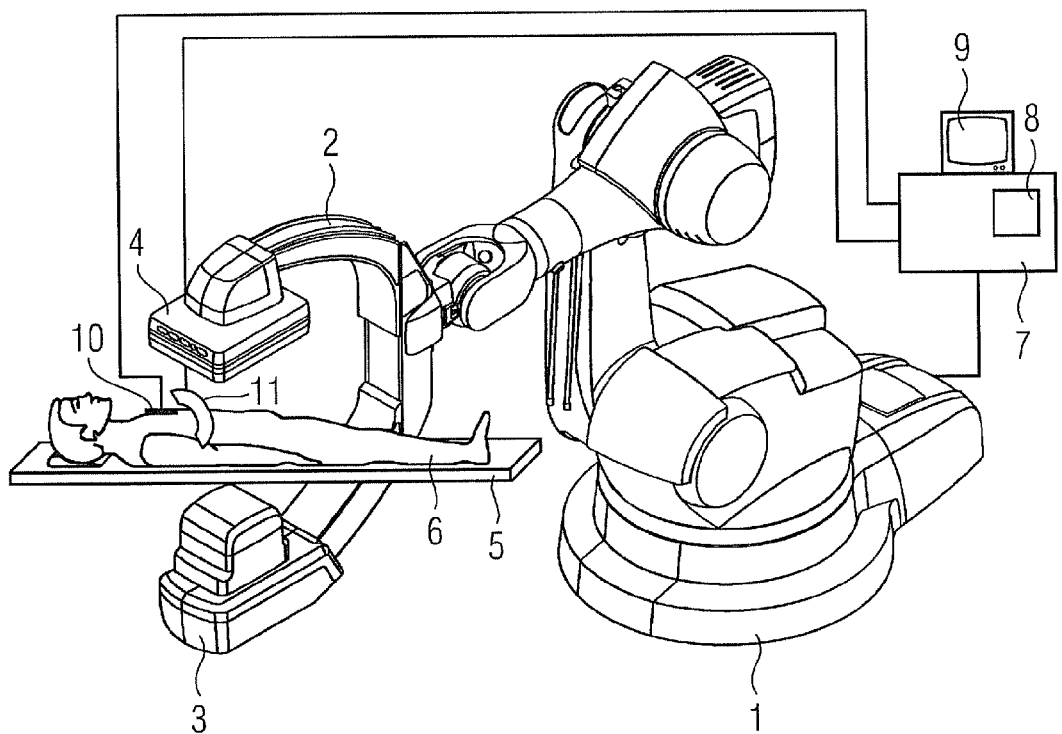
FIG. 1 shows a known X-ray C-arm system for radiology, cardiology or neurosurgery having an industrial robot as carrier device.
Figure 2:
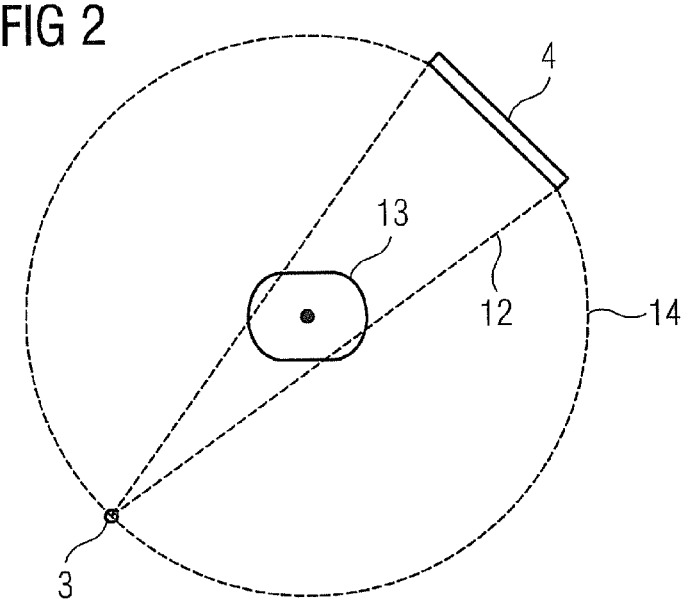
FIG. 2 shows a view of the path of a detector and a radiation source according to FIG. 1 around an examination subject in the axial viewing direction.
Figure 3:
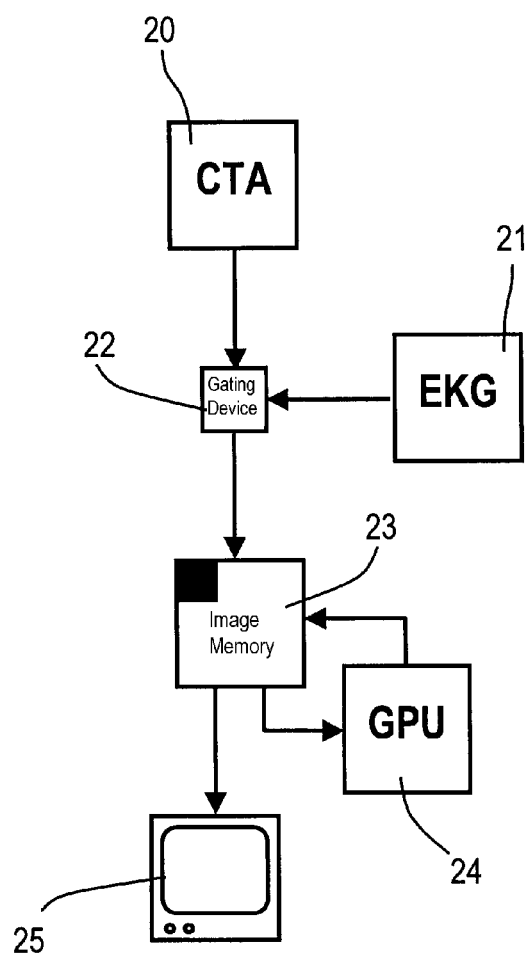
FIG. 3 shows the inventive method for visualizing images.

FIG. 3 shows an ACT X-ray system 20 for angiography CT and an ECG device 21 which controls the data flow of the ACT X-ray system 20 by means of a gating device 22. Connected to the gating device 22 is an image memory 23 in which initially a recorded 3D image data set is stored from which, following the acquisition of the complete 3D image data set, a 3D reconstruction image is computed by a GPU 24 and is then likewise stored in the image memory 23. The GPU 24 also initiates a motion estimation which will be described further below. The reconstructed and processed 3D images are displayed on the monitor 9 by means of a 3D playback device 25.

FIG. 4 shows method steps of an embodiment of the method according to the invention:

A first step (G1), recording of a projection image data set and e.g. an ECG; a second step (G2), calculation of a reference image with ECG gating and affine motion correction; and a third step (G3), 3D image reconstruction through correction of the elastic motion with use of all of the data.

The second step (G2) for determining the affine motion parameters can be subdivided e.g. as follows:

(A1) Morphological filtering (preprocessing) of the projection image data set,
(A2) statistical selection of an affine motion parameter,
(A3) calculation of the gradient by means of finite differences, e.g. u0+du, u0−du,
(A3.1) calculation of 3D images by means of ECG gating and modified affine motion parameters,
(A3.2) forward projection of the 3D images,
(A3.3) calculation of the quality function, in this case mean value of the normalized cross-correlation function (NCC),
(A3.4) calculation of the gradient of the quality function,
(A4) calculation of the optimized affine motion parameter from the gradient of the quality function, and
(A5) repetition from (A2) until the convergence is fulfilled.

The present patent application takes into account non-periodic motions in a reconstruction using ECG gating. The complexity of the poorly formulated problem is reduced in that the periodic cardiac motion is already taken into consideration by means of the ECG gating. The remaining, non-periodic motion can be described by means of simple motion models. For example, patient motion and respiration can be described essentially by means of translation and rotation. It should be possible to describe arrhythmic cardiac motion by means of affine models.

The 3D image reconstructed by means of ECG gating and simple, non-periodic motion compensation can be used as an a priori 3D image for the methods described in E. Hansis et al [5] and C. Rohkohl et al [6]. Both the a priori 3D image and the 3D image of the main reconstruction are corrected in this way for non-periodic motion.

The method according to the invention can also estimate and correct non-periodic motion from the 2D recording data of a tomographic acquisition. Non-periodic motions frequently occur in the clinical environment. Arrhythmic cardiac motions, respiration and patient motion are frequently observed in the case of DynaCT cardiac acquisitions of 5 s recording duration. Previously these motions could not be corrected and led in part to considerable losses in image quality. Occasionally recordings were unusable due to the patient's respiratory motions. The method according to the invention leads to an improvement in image quality by taking into account a variable heart rhythm (arrhythmic cardiac motion) and can also compensate for respiratory motion and patient motion.

According to the invention an affine motion model is used in which a motion estimation is formulated as an optimization problem. A search is made for an affine motion by means of which a motion-corrected 3D image can be reconstructed whose forward projection has maximum convergence with the recorded 2D projection images. A morphological top-hat filter [2] is applied to the 2D projection data in order to reduce anatomical noise (structures that are not vessels).

The invention relates to a motion-compensated controlled reconstruction algorithm which consists of a time-continuous affine 4D motion model which is capable of reconstructing data sets containing a high level of non-periodic motion patterns. A time-correlated target function is introduced which measures the disturbance between the measured projection data and the dynamic forward projection of the motion-compensated controlled reconstruction. The results show that the algorithm according to the invention delivers excellent reconstruction quality in the cases where classical approaches achieve only diminished image quality.

The quality of the ECG-controlled reconstructions is dependent to a high degree on the periodicity of the motion. If the physical motion state of the heart fluctuates for the scanned heartbeats, this poses a problem for reconstruction algorithms that are based on a periodicity. Two main sources of non-periodicity can be identified. Firstly, for different pulses, i.e. arrhythmias, the ECG phases cannot be referred to one another precisely with a physical motion state of the heart. Secondly, a motion due to respiration adds a component of a second motion which leads to a non-periodic motion. However, it has been shown in preceding examinations that changes in the cardiac phases and respiratory motions of cardiac blood vessels can be modeled using global transformations, e.g. rigid-body transformations or affine transformations. Affine transformations can in this case effect more than just a transformation of a rigid body: scaling and shearing are also included in addition to the translation and rotation (in the case of the rigid body). An algorithm for estimating such an affine motion between the different heartbeats is presented in the following sections.

A time-continuous motion model is assumed in which a voxel $x=(x_0, x_1, x_2)^T$ is mapped to a new voxel position x' each time a projection image is acquired. It is expressed by means of a function $$M: N \times R^3 \times S \mapsto R^3 \text{ where } M(i,x,s)=x'$$

which converts the voxel coordinate x at the point in time of the i-th projection image. The diagram is based on the parameters of the motion model. A global affine motion model is used in this work.

For this purpose a set of time instants is generated. Each time instant is assigned to twelve affine parameters which describe the affine transformation at this moment. The set of time instants is determined by the ECG signal. We select two time instants per heartbeat. These are in particular the reference cardiac phase $h_r$ and an additional cardiac phase $h_r+\Delta h_r$. A nearest-neighbor gating is performed for both cardiac phases, i.e. only the projection that is nearest to the desired point in the cardiac cycle for each acquired heartbeat is preselected. For a cardiac phase h this set of projection images is designated by $N_h$. The complete set L of the temporal control points is then given by $$L=\{1,N\} \cup N_{h_r} \cup N_{h_r+\Delta h_r}, \quad (1)$$

where the number of projections lies in the range from 1 to N. The first and last projection image are added in such a way that no boundary problems occur.

The affine parameters $s_l \in R^{12}$ for an individual time instant $l \in L$ are a vector with twelve elements having the following components:

$$s_l=(t_0,t_1,t_2,\alpha_0,\alpha_1,\alpha_2,a_0,a_1,a_2,b_0,b_1,b_2)^T$$

where $t_i$ represents the translation according to the length, $\alpha_i$ the rotation around, $a_i$ the scaling along, and $b_i$ the shearing of the i-th coordinate axis. The complete parameter vector $s \in S$, $S=R^{12|L|}$ is then given by $$s=(s_{L_1}, \ldots, s_{L_{|L|}}) \quad (2)$$

with $L_i$ as the i-th, smallest element of L.

For an arbitrary projection image i the affine transformation parameters are achieved by interpolation in time of each component. A cubic B-spline interpolation is advantageously used.

The concluding motion model is then given formally by $$M(i, x, s) = x' \text{ where } A_{\tilde{s}_i}\begin{pmatrix} x \\ 1 \end{pmatrix} = \begin{pmatrix} x' \\ 1 \end{pmatrix} \quad (3)$$

where $A_{\tilde{s}_i}$ is the affine transformation matrix in the homogeneous coordinates for the affine parameters.

Motion-Compensated ECG-controlled Reconstruction
Projection Image Preprocessing:

Only the motion of the cardiac blood vessels is of interest for motion estimation according to the invention. For this reason a background reduction technique proposed in Hansis et al [2] is applied. The remaining blood vessels and the background are removed to a large degree through the use of a morphological top-hat filter. In the following this preprocessed projection data is described by means of the function $$p: N \times R^2 \mapsto R$$

where p(i, u) inverts the value of the preprocessed i-th projection image at the pixel u.

Reconstruction Algorithm:

A dynamic reconstruction algorithm f(x,s) is defined for motion estimation and correction. The function f returns the reconstructed object value at a voxel x based on the parameters s of the motion model. In principle any dynamic reconstruction algorithm can be used. According to the invention an extension of the Feldkamp-David-Kress algorithm (FDK reconstruction method) described in Schäfer et al [1] is used for the motion of objects. The ECG gating is performed by applying a weighting factor λ at each image which is calculated from the relative distance to the reference cardiac phase. The dynamic ECG-controlled FDK reconstruction $f_{h_r}: R^3 \times S \mapsto R$ is then given by $$f_{h_r}(x,s) = \Sigma_i \lambda(i,h_r) \cdot w(i,M(i,x,s)) \cdot p_F(i,A(i,M(i,x,s))). \quad (4)$$

The function $w: N \times R^3 \mapsto R$ is the distance weighting of the FDK formula. The preprocessed, filtered and redundancy-weighted projection data is achieved by means of the function $p^F: N \times R^2 \mapsto R$, where $p^F(i,u)$ represents the value of the i-th image at the pixel u. The pixel position u is determined by means of the perspective projection $A: N \times R^3 \mapsto R^2$, where the function A(i,x)=u maps a voxel x onto a pixel position u in the i-th projection image.

The function λ is a weighting function used for obtaining an ECG-phase-correlated reconstruction for the cardiac phase $h_r \in [0,1]$. It is given by $$\lambda(i, h_r) = \begin{cases} \cos^\beta\left(\frac{d(h(i), h_r)}{\omega}\pi\right) & \text{if } d(h(i), h_r) \leq \frac{\omega}{2} \\ 0 & \text{else} \end{cases} \quad (5)$$

where h(i) is the cardiac phase of the i-th projection image and $\omega \in (0,1]$ is the width of the non-zero support region of the weight function. The parameters $\beta \in [0, \inf)$ control the shape of the support region, a value of zero corresponding for example to a rectangular shape. The function d is a distance function which measures the distance between two motion phases. It is defined for a relative cardiac phase as follows $$d(h1,h2)=\min_{c \in \{0,1,-1\}} |h_1-h_2+c|.$$

Target function for motion estimation

The motion estimation is formulated as a multidimensional optimization problem, where the motion model parameters $\hat{s} \in S$ which maximize the target function $L: S \mapsto R$ must be estimated, i.e.

$$\hat{s} = \underset{s \in S}{\operatorname{argmax}} L(s) \quad (6)$$

The target function according to the invention is motivated by the fundamental relationship of the motion-compensated reconstruction f with the measured projection data p. Maximum intensity projections of a reconstruction f(x,s) can be generated by means of the dynamic forward projection:

$$r(i, u, s) = \max_{x \in L_{i,u}} f_{h_r}(M^{-1}(i, x, s), s) \quad (7)$$

The function $r: N \times R^2 \times S \mapsto R$ represents the forward projection of the dynamic maximum intensity of the ECG-controlled and motion-compensated reconstruction $f_{h_r}$. The voxels on the straight measurement beam $L_{i,u}$ of the i-th image which strikes the detector at pixel u are transformed by the inverse motion model in order to consider the motion state at the projection image i.

The synchronization of the measured and edited data p and the forward-projected data r is calculated by means of the averaged normalized cross-correlation (NCC). The target function is formally yielded by:

$$L(s) = \frac{1}{v} \sum_i^N \left( \lambda(i, h_r) \sum_u \frac{(p(i, u) - \mu_{p_i})(r(i, u, s) - \mu_{r_{i,s}})}{\sigma_{p_i} \sigma_{r_{i,s}}} \right) \quad (8)$$

with the normalization factor $v=(I_p-1)\Sigma_i^N \lambda(i, h_r)$, where $I_p$ is the number of image pixels u of a projection and μ, σ are the mean and standard deviation, respectively, of the indexed image. The value of the range $L(s)\epsilon[-1,1]$ of the target function with the maximum value represents a complete linear relationship between the measured and forward-projected data. The NCC of the i-th projection image pairs is weighted by means of the gating function λ as it characterizes the effect on the dynamic ECG-controlled reconstruction.

Optimization Strategy:

A stochastic slope curve method is applied for maximizing equation (8). A specific probability is preselected in each repetition of one of the twelve affine parameters. For initialization, all parameters are assigned the same probability. The slope is calculated using the finite differences in that the specified parameters for all time instants are changed. Initially a step in the slope direction is undertaken with a specified increment size. The probability of the parameter preselected in the following repetition is set proportionally to the increase in the cost function value. The optimization stops after several repetitions or if the convergence ratio falls below a certain threshold.

This type of stochastic selection of the parameters for the gradient-based optimization method has the benefit that the most advantageous parameters are selected. In this way a rapid convergence is found with only a minimum number of cost function analyses. This applies particularly because mainly the non-periodic parts of the motion are caused by the translation or rotation components which are preferred during the optimization if they obtain a greater gain in the target function value.

Implementation Details:

An evaluation of the target function according to equation (8) includes an ECG-controlled reconstruction, an ECG-controlled forward projection and the calculation of a quality metric. Each step can be very effectively executed in parallel on a graphics card, as described in Scherl et al [7] for example. The algorithm can be executed on graphics processors (Graphics Processor Units (GPUs)) using so-called CUDA programming. The back-projection of the FDK reconstruction and the forward projection are based on projection matrices. The affine matrix $A_{s_j}$ according to equation (3) is dependent only on the projection geometry and is independent of the voxel position. This enables the voxel-by-voxel calculation of the motion transformation M to be replaced by a multiplication of the projection matrix by the affine transformation matrix. As a result no additional overhead is introduced during the forward- or backward-projection operations.

Non-periodic motion is an important clinical challenge of the C-arm reconstruction of cardiac blood vessels. By means of the ECG-controlled 3D reconstruction with affine motion correction for non-cyclical motions the method according to the invention is able to realize a perfect reconstruction of data sets for which traditional approaches fail.

A method for three-dimensional visualization of a moving structure by means of a rotation angiography method is described in which a series of projection images is recorded from different recording angles by an image acquisition unit during a rotation cycle for the purpose of 3D data acquisition, wherein three-dimensional image data can be reconstructed from the projection images, said method comprising the following steps: performance of a continuous rotation cycle with ECG-triggered control of the 3D data acquisition (ECG gating); motion estimation for motion-corrected 3D image reconstruction whose forward projection exhibits maximum convergence with the recorded 2D projection images, simple motion models being described; and reconstruction of the three-dimensional image data from the data acquired during the rotation cycle with the motion-corrected image data.

The method according to the invention has, as important components, generation of a provisional 3D image (reference image) with initial correction of the motion by means of affine transformations, and generation of a definitive 3D image using the reference image while correcting the motion by means of elastic deformations.

References

[1] D. Schäfer, J. Borgert, V. Rasche, and M. Grass, "Motion-compensated and gated cone beam filtered back-projection for 3D rotational x-ray angiography", IEEE Transactions on Medical Imaging, vol. 25, no. 7, pp. 898-906, July 2006.

[2] E. Hansis, D. Schafer, O. Dossel, and M. Grass, "Evaluation of iterative sparse object reconstruction from few projections for 3D rotational coronary angiography", TREE Transactions on Medical Imaging, vol. 27, no. 11, pp. 1548-1555, November 2008.

[3] C. Blondel, G. Malandain, R. Vaillant, and N. Ayache, "Reconstruction of coronary arteries from a single rotational x-ray projection sequence", IEEE Transactions on Medical Imaging, vol. 25, no. 5, pp. 653-663, May 2006.

[4] E. Hansis, H. Schomberg, K. Erhard, O. Dössel, and M. Grass, "Four-dimensional cardiac reconstruction from rotational x-ray sequences: first results for 4d coronary angiography", E. Samei and J. Hsieh, Eds., vol. 7258, no. 1. Lake Buena Vista, Fla., USA: SPIE, March 2009, p. 72580B.

[5] E. Hansis, D. Schäfer, O. Dössel, and M. Grass, "Projection-based motion compensation for gated coronary artery reconstruction from rotational x-ray angiograms", Physics in Medicine and Biology, vol. 53, no. 14, pp. 3807-3820, July 2008.

[6] C. Rohkohl, G. Lauritsch, M. Prümmer, and J. Hornegger, "Interventional 4-d motion estimation and reconstruction of cardiac vasculature without motion periodicity assumption", in Medical Image Computing and Computer-Assisted Intervention—MICCAI 2009, Series Lecture Notes in Computer Science, G.-Z. Yang, D. Hawkes, D. Rueckert, A. Noble, and C. Taylor, Eds., vol. 5761. Springer, 2009, pp. 132-139.

[7] H. Scherl, B. Keck, M. Kowarschik, and J. Hornegger, "Fast GPU-Based CT Reconstruction using the Common Unified Device Architecture (CUDA)", in Nuclear Science Symposium, Medical Imaging Conference 2007, E. C. Frey, Ed., 2007, pp. 4464-4466.

The invention claimed is:

1. A method for three-dimensionally imaging a moving structure, comprising:
   recording a series of projection images by an image acquisition unit from different recording angles during a continuous rotation cycle with simultaneous recording an ECG;
   generating a three-dimensional reconstructed reference image of the moving structure from the projection images with an initial correction of a motion of the moving structure by affine transformations, wherein the three-dimensional reconstructed reference image is generated based on non-periodic motion of the moving structure;

generating a motion-compensated three-dimensional reconstruction image data of the moving structure using the three-dimensional reconstructed reference image while performing an estimation and correction of the motion of the moving structure by elastic deformations, wherein the motion of the moving structure is estimated and corrected using the three-dimensional reconstructed reference image based on non-periodic motion of the moving structure, generating a set of time instants assigned to twelve affine motion parameters of an affine motion model that describe the affine transformations at the time instants;

optimizing the estimation of the motion using the affine motion model; and generating a target function based on a relationship of the motion-compensated three-dimensional reconstruction image data with the recorded projection images, wherein the optimizing comprises:
  selecting the affine motion parameters;
  calculating a quality function; and
  optimizing the affine motion parameters, wherein the affine motion parameters are statistically selected, wherein the affine motion parameters are initially assigned with same probability, and wherein probabilities of the affine motion parameters in a following repetition are preselected so that the affine motion parameters of the non-periodic motion of the moving structure are selected during the optimization, and wherein the affine motion parameters of the non-periodic motion of the moving structure are selected in the following repetition if the affine motion parameters of the non-periodic motion of the moving structure obtain a greater gain in the target function.

2. The method as claimed in claim 1, wherein a morphological filter is applied to the projection images for reducing an anatomical noise.

3. The method as claimed in claim 2, wherein the filter is a top-hat filter.

4. The method as claimed in claim 1, wherein the motion comprises a motion of a patient and respiration of the patient and is described by a motion model with translation and rotation.

5. The method as claimed in claim 1, wherein an arrhythmic cardiac motion is described by an affine motion model.

6. The method as claimed in claim 1, wherein a motion field in the three-dimensional reconstructed reference image is estimated directly by iteratively comparing a forward projection of the three-dimensional reconstructed reference image with the projection images.

7. The method as claimed in claim 1, wherein three-dimensional images are calculated and forward projected with ECG gating and the affine motion parameters, and wherein the quality function is calculated by normalized cross-correlation between the forward projected three-dimensional images and the recorded projection images.

8. The method as claimed in claim 1, wherein the affine motion parameters are optimized from gradient of the quality function.

* * * * *